United States Patent
Bollag et al.

(10) Patent No.: US 6,610,742 B1
(45) Date of Patent: Aug. 26, 2003

(54) TREATMENT OF T-HELPER CELL TYPE 2-MEDIATED IMMUNE DISEASES BY RETINOID ANTAGONISTS

(75) Inventors: Werner Bollag, Basel (CH); Michael Klaus, Weil am Rhein (DE); Paola Panina-Bordignon, Milan (IT); Francesco Sinigaglia, Milan (IT)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/631,655

(22) Filed: Aug. 3, 2000

Related U.S. Application Data

(62) Division of application No. 09/189,189, filed on Nov. 10, 1998, now Pat. No. 6,133,309.

(30) Foreign Application Priority Data

Nov. 12, 1997 (EP) ............................................. 97119776

(51) Int. Cl.⁷ ............................................. A61K 31/20
(52) U.S. Cl. ...................................................... 514/560
(58) Field of Search ........................................ 514/560

(56) References Cited

U.S. PATENT DOCUMENTS

| | | | |
|---|---|---|---|
| 5,391,766 A | 2/1995 | Klaus et al. | 549/23 |
| 5,512,683 A | 4/1996 | Klaus et al. | 549/9 |
| 5,547,983 A | 8/1996 | Charpentier | 514/535 |
| 5,705,167 A | 1/1998 | Bernardon et al. | 514/523 |
| 5,801,253 A | 9/1998 | Klaus et al. | 549/23 |
| 5,986,131 A | 11/1999 | Klaus et al. | 549/23 |

FOREIGN PATENT DOCUMENTS

| | | | | |
|---|---|---|---|---|
| EP | 0568898 | 4/1993 | | C07D/335/06 |
| EP | 0661259 | 7/1995 | | C07C/233/81 |
| EP | 0740937 | 11/1996 | | A61K/311/38 |
| WO | 92 19583 | 11/1992 | | C07C/65/28 |
| WO | 94 14777 | 7/1994 | | C07D/231/54 |
| WO | WO 9533745 | 12/1995 | | C07D/409/04 |
| WO | 97 09297 | 3/1997 | | C07C/69/78 |
| WO | WO 97/12853 | * 4/1997 | | C07C/59/72 |
| WO | 97 12853 | 4/1997 | | C07C/59/72 |
| WO | 97 13505 | 4/1997 | | A61K/31/19 |
| WO | WO 9825875 | 6/1998 | | C07C/63/66 |
| WO | WO 9846228 | 10/1998 | | A61K/31/445 |

OTHER PUBLICATIONS

Cantorna et al, Eur. J. Immunol., vol. 25, pp. 1673–1679, 1995.*
Apfel et al, P.N.A.S., vol. 80, pp. 7129–7133, Aug. 1992.*
Lee et al., The Journal of Biological Chemistry, 271:11897–11903 (1996).
Romagnani, Annu. Rev. Immunol., 12, 227–257 (1994).
Robinson et al, Chem. Immunol., 63:187–203 (1996).
Abbas et al., Nature, 383:787–793 (1996).
Kips et al., Am. J. Respir. Crit. Care Med., 153:535–539 (1996).
Apfel et al., Proc. Natl. Acad. Sci., 89, pp 7129–7133 (1992).
Racke et al., The Journal of Immunology, 154, pp 450–458 (1995).
Pfahl et al., Vitamins and Hormones, 49, 327–382 (1994).
Brinckerhoff et al., Science, 221, pp 756–758 (1983).
Massacesi et al., J. Clin. Invest., 88, pp 1331–1337 (1991).
Derwent Abstract 010990246 relates to EP 0740937.
European Journal of Immunology, vol. 25, (6), pp. 1673–1679 (1995).
Derwent Abstract 010990246 relates to EP 0740937.

* cited by examiner

*Primary Examiner*—Russell Travers
(74) *Attorney, Agent, or Firm*—George W. Johnston; John P. Parise

(57) ABSTRACT

Retinoids with retinoid receptor antagonistic activity, pharmaceutically acceptable salts and pharmaceutically acceptable hydrolyzable esters thereof, have been found efficacious in treating T-helper cell type 2 (Th2)-mediated immune diseases, such as immunoglobulin E (IgE)-mediated allergic diseases.

19 Claims, No Drawings

TREATMENT OF T-HELPER CELL TYPE 2-MEDIATED IMMUNE DISEASES BY RETINOID ANTAGONISTS

CROSS REFERENCE TO RELATED APPLICATION

This is a divisional of patent application Ser. No. 09/189,189, filed Nov. 10, 1998 now U.S. Pat. No. 6,133,309 which claims priority to European Patent 97/119 776.9 filed Nov. 12, 1997.

BACKGROUND OF THE INVENTION

1. Field

The present invention relates a method for using retinoid antagonists, such as retinoids with selective Retinbic Acid Receptor ("RAR") antagonistic activity, Retinoid X Receptor ("RXR") antagonistic activity or mixed RAR-RXR antagonistic activity, to treat T-helper cell type 2 ("Th2")-mediated immune diseases. Th2-mediated immune diseases include immunoglobulin E ("IgE")-mediated allergic diseases. The present invention also relates to using retinoid antagonists to prepare medicaments for treating Th2-mediated immune diseases.

2. Description

Retinoids are a class of compounds structurally related to vitamin A and include natural and synthetic compounds. Retinoids are clinically useful in the treating dermatological and oncological diseases.

Retinoid activity is thought to be mediated by the nuclear retinoid receptors RARα, β, γ and RXRα, β, γ, belonging to the superfamily of steroid, thyroid hormone, vitamin D, peroxisome proliferator-activated receptors [Pfahl et al., *Vitamins and Hormones*, 49: 327–382 (1994)]. Retinoids with receptor agonistic activity bind to and activate receptors, whereas retinoids with receptor antagonistic activity bind to receptors but do not activate them.

Experimentally, retinoids with retinoid receptor agonistic activity have been shown to be active in model systems for treating dermatological and oncological diseases and in models for treating immunological diseases. Retinoids with retinoid receptor agonistic activity have been shown active in treating adjuvant arthritis [Brinckerhoff et al., *Science*, 221: 756–758 (1983)] and experimental allergic encephalomyelitis [Massacesi et al., *J. Clin. Invest.*, 88: 1331–1337 (1991); Racke et al., *J. Immunol.*, 154, 450–458 (1995)], animal models for rheumatoid arthritis and multiple sclerosis, respectively. Both diseases are considered to belong to Th1-mediated immune diseases.

Experimentally, retinoids!with retinoid receptor antagonistic activity (retinoid antagonists) have been shown effective in counteracting many properties of retinoids with retinoid receptor agonistic activity (retinoid agonists), such as inhibiting cell proliferation, inducing cell differentiation, inducing apoptosis and inhibiting angiogenesis [Bollag et al., *Int. J. Cancer*, 70: 470–472 (1997)]. Retinoid antagonists also suppress toxic side effects of retinoid agonists, such as the signs and symptoms of the hypervitaminosis A syndrome and teratogenesis [Standeven et al., *Toxicol. Appl. Pharmacol.*, 138: 169–175 (1996); Eckhardt and Schmitt, *Toxicol. Letters*, 70: 299–308 (1994)]. Therefore, they may be useful clinically in preventing or treating adverse events caused by retinoid agonists.

Retinoid antagonists have been proposed for clinical use in the prevention and treatment of retinoid-induced toxicity and side effects, particularly of the so-called hypervitaminosis A syndrome. Retinoid antagonists have also been proposed to be used in combination with retinoid receptor agonists or other nuclear receptor agonists for preventing and treating preneoplastic or neoplastic lesions, vitreoretinopathy, and retinal detachment. In addition, retinoid antagonists may be useful as single agents, based on their anti-proliferative effect, for treatment of certain neoplasms insensitive to retinoid receptor agonists [WO 97/09297].

The subject invention provides for the first time a method for using retinoid antagonists in the treatment of Th2-mediated immune diseases, such as IgE-mediated allergic diseases and diseases mediated by the Th2-related cytokines.

SUMMARY OF THE INVENTION

The subject invention provides a method of treating a T-helper cell type 2-mediated immune disease or a disease mediated by T-helper cell type 2-related cytokines. This method comprises administering to a subject having a T-helper cell type 2-mediated immune disease or a disease mediated by T-helper cell type 2-related cytokines an effective amount of a compound selected from the group consisting of retinoid antagonists, pharmaceutically acceptable salts of retinoid antagonists, and pharmaceutically acceptable hydrolyzable esters of such retinoid antagonists and their salts.

DETAILED DESCRIPTION OF THE INVENTION

The subject invention will now be described in terms of its preferred embodiments. These embodiments are set forth to aid in understanding the invention but are not to be construed as limiting.

In the scope of the present invention the term "retinoid antagonists" is used for retinoids or compounds with RAR, RXR or mixed RAR-RXR antagonistic activity. It includes compounds with receptor neutral antagonistic activity (neutral antagonists), receptor inverse agonistic activity (inverse agonists) and negative hormone activity (negative hormones) [Klein et al., *J. biol. Chem.*, 271: 22692–22696 (1996)].

In the scope of the present invention the term "retinoid antagonists" encompass compounds of formulas I–XVI depicted below:

a) RAR α-antagonists of formulas:

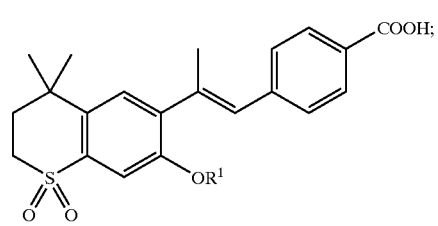

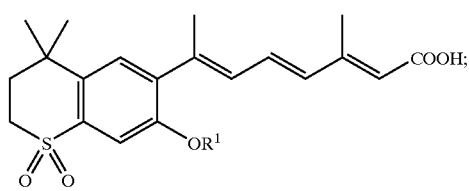

-continued

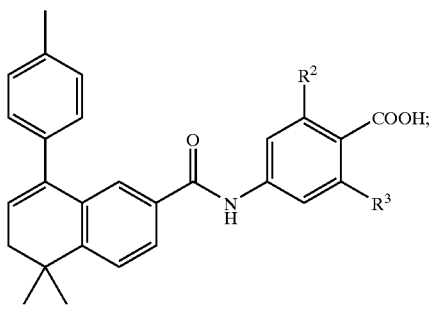
III

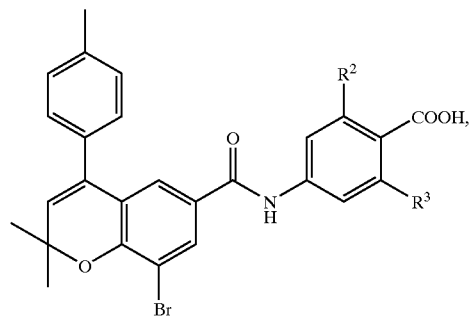
IV wherein R¹ is $C_{5-10}$-alkyl, and $R^2$ and $R^3$ independently of each other are hydrogen or fluorine;
such compounds are described in U.S. Pat. No. 5,391,766 and *J. Med. Chem.*, 40: 2445 (1997);

b) RAR α, β antagonists of formulas:

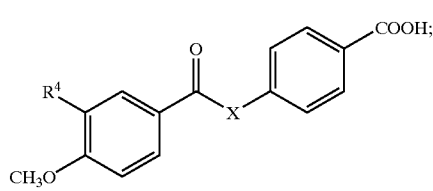
V

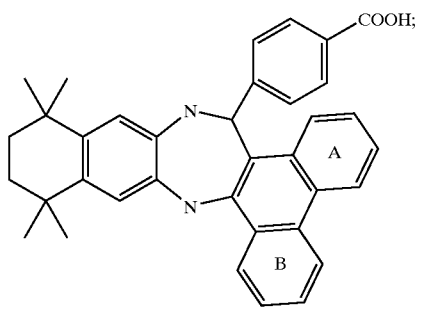
VI

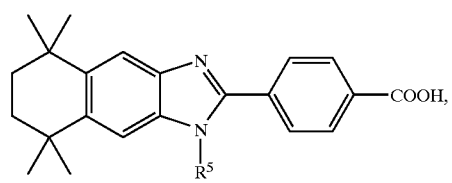
VII wherein $R^4$ is diamantyl, X is O or NH, $R^5$ is phenyl or benzyl, and
wherein optionally either ring A or ring B is present;
such compounds are described in *Med. Chem. Res.*, 1: 220 (1991); *Biochem. Biophys. Res. Com.*, 231: 243 (1997); and *J. Med. Chem.*, 37: 1508 (1994);

c) RAR β, γ antagonists of formula

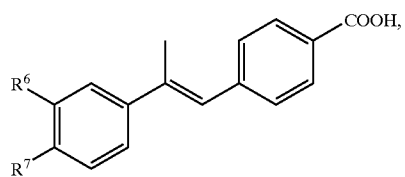
VIII wherein $R^6$ and $R^7$ independently of each other hydroxy, $C_{1-4}$-alkoxy, optionally branched $C_{1-5}$-alkyl or adamantyl;
such compounds are described in *J. Med. Chem.* 38: 4993 (1995);

d) RAR γ antagonists of formulas:

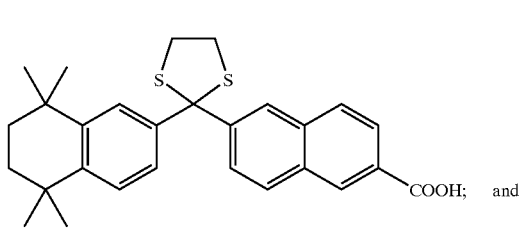
IX

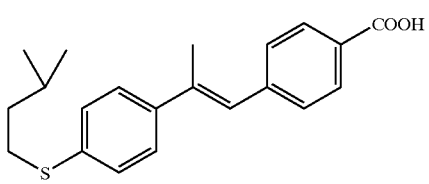
X such compounds are described in *Cancer Res.*, 55: 4446 (1995);

e) RAR α, β, γ antagonists of formulas:

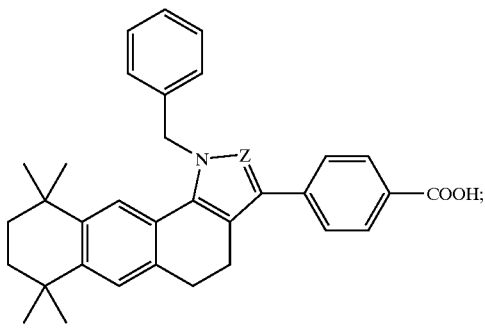
XI

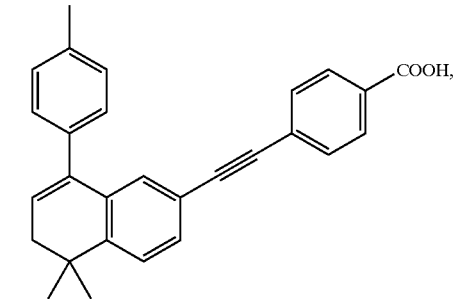
XII

-continued

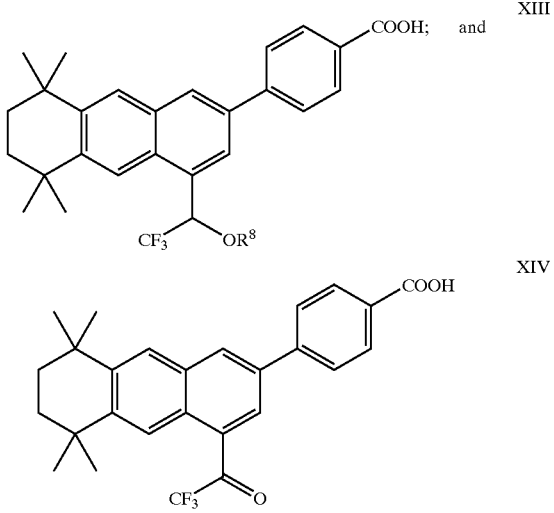

wherein Y is —CH$_2$— or sulfur and Z is —CH= or nitrogen, and R$^8$ is hydrogen or C$_{1-4}$-alkyl;

such compounds are described in *J. Med. Chem.* 38: 3163 and 4764 (1995); *J. Biol. Chem.*, 271: 11897 and 22692 (1996);

f) RXR antagonists of formulas:

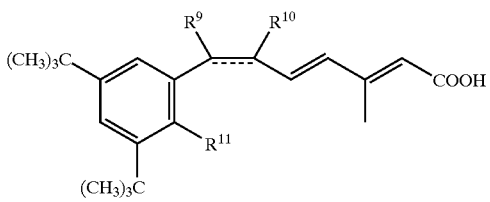

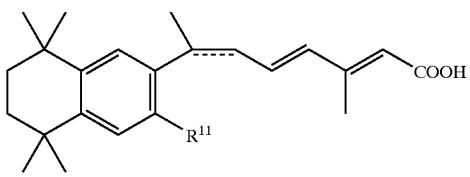

wherein the dotted bond is optional; and, when the dotted bond is present, R$^9$ is methyl and R$^{10}$ is hydrogen; and, when the dotted bond is absent, R$^9$ and R$^{10}$ taken together are methylene to form a cis-substituted cyclopropyl ring; R$^{11}$ is C$_{1-4}$-alkoxy;

such compounds are described in EP Patent Appl. No. 97 107 843.1; *J. Med. Chem.*, 39: 3229 (1996); and *Nature*, 383: 450 (1996).

In accordance with this invention, it has thus been found that administration of retinoid antagonists, pharmaceutically acceptable salts, and pharmaceutically acceptable hydrolyzable esters thereof, are efficacious in treating patients with T-helper cell type 2 (Th2)-mediated diseases. It has also been found that the administration of retinoid antagonists is efficacious in treating patients with diseases mediated by Th2-related cytokines, such as interleukin-4 (IL4) and IL-5.

The invention, therefore, in one aspect, relates to the use of retinoid antagonists, their pharmaceutically acceptable salts or pharmaceutically acceptable hydrolyzable esters, for the manufacture of a medicament for the treatment of T-helper cell type 2 (Th2)-mediated immune diseases. In another aspect the invention relates to the use of retinoid antagonists, their pharmaceutically acceptable salts or pharmaceutically acceptable esters thereof for the manufacture of a medicament for the treatment of disease mediated by Th2-related cytokines, such as IL4 and IL-5.

The invention also relates to a method for treating patients having T-helper cell type 2 (Th2)-mediated immune diseases comprising administering to said human patient a compound selected from the group of retinoid antagonists, pharmaceutically acceptable salts and pharmaceutically acceptable hydrolyzable esters thereof, said compound being administered in an amount effective to treat said disease. The term "treatment" or "treating" includes preventive and/or therapeutic treatment.

As used herein, the term "T-helper cell type 2-mediated immune diseases" relates to diseases involving immunoglobulin E (IgE) and mast cells due to the development and activation of allergen-specific Th2 cells and it encompasses alergic diseases, such as atopic dermatitis, other dermatological diseases associated with atopy; allergic rhinitis or hay fever, allergic bronchial asthma in its acute or chronic, mild or severe forms, with or without acute or chronic bronchitis. Elevated serum levels of immunoglobulin E (IgE) and hypereosinophilia can be associated with these diseases. Retinoid antagonists are effective in all those immune diseases which are linked with an increase of Th2 cell activity and an increased secretion of the related cytokines, such as IL-4 and IL-5. The therapeutic effect of retinoid antagonists is due to a decrease in Th2 cell activity, a decreased secretion of the related cytokines, such as IL-4 and IL-5, and/or an increase in Th1 cell activity due to the enhancement of IL-12 production by activated myelomonocytic cells. [S. Romagnani, Ann. *Rev. Immunol.*, 12: 227–257 (1994); Romagnani, ed., *Th1 and Th2 Cells in Health and Disease. Chem. Immunol.*, Karger, Basel, 63: 187–203 (1996); Abbas et al., *Nature*, 383: 787–793 (1996)].

The efficacy of the retinoid antagonists in accordance with the present invention can be shown by their ability to either upregulate Th1 cell activity or induce/stimulate the production of cytokines, such as IL-12, IFNγ, TNF; and/or downregulate Th2 cell activity, or inhibit the production of cytokines, such as IL-4 and IL-5.

Retinoid antagonists are active in the treatment of allergic bronchial asthma. The hallmarks of inflammation associated with asthmatic disease are the presence of activated eosinophils, an increased sensitivity of the airways (hyperresponsiveness), edema, mucus hypersecretion and cough. This inflammatory process is mediated by the generation and activation of Th2-type cells. The ability of retinoid antagonists to promote a Th1-type response and thereby to suppress the Th2-type response is thought to be the mechanism underlying the efficacy of these compounds in allergic lung inflammation/asthma. Retinoid antagonists are acting on Th1-type cells, in inhibiting the signs and symptoms of allergic lung inflammation/asthma [Gavett et al., *J. Exp. Med.*, 182: 1527–1536 (1995); Kips et al., *Am. J. Respir. Crit. Care Med.*, 153: 535–539 (1996)]. They are active in antigen/allergen (e.g. ovalbumin)-sensitized and challenged animals. Retinoid antagonists, given either systemically or topically by aerosol, are efficacious in attenuating, inhibiting or reversing bronchoconstriction, airway edema and mucus hypersecretion, airway inflammation, accumulation of eosinophils and neutrophils in the broncho-alveolar tissue and broncho-alveolar lavage respectively, as well as airway hyperresponsiveness to non-specific stimuli.

For the treatment, the active compound, i.e. a retinoid antagonist, a pharmaceutically acceptable salt or a pharmaceutically acceptable hydrolyzable ester thereof, is administered either systemically or topically. Preferably, said compound is administered as a composition containing said active compound and a pharmaceutically acceptable carrier or diluent compatible with said active compound. In preparing such composition, any conventional pharmaceutically acceptable carrier can be utilized. When the drug is administered orally, it is generally administered at regular intervals, conveniently at mealtimes or once daily. It has been established that this compound is effective in doses which show no or only mild side effects when given orally or when given topically. Therefore, oral or topical administration of the active compound is generally preferred. For treating diseases of the skin, mouth, nose, pharynx, larynx, bronchus etc. oral combined with topical administration may also be used advantageously.

In the treatment of T-helper cell type 2-mediated immune diseases, retinoid antagonists, when administered orally do not or not significantly induce the adverse events belonging to the toxic syndrome of hypervitaminosis A, such as mucocutaneous, musculoskeletal, neurologic manifestations and elevation of transaminases, triglycerides and cholesterol. In addition, they are not or less teratogenic in contrast to the receptor agonistic retinoids clinically useful in the treatment of dermatological and oncological diseases, such as all-trans retinoic acid (tretinoin), 13-cis retinoic acid (isotretinoin), etretinate and acitretin.

In the treatment of T-helper cell type 2-mediated immune diseases, retinoid antagonists, pharmaceutically acceptable salts or pharmaceutically acceptable hydrolyzable esters thereof, can be used alone or in combination with other measures, e.g. in combination with other pharmaceutically active substances such as topical or systemic corticosteroids, antihistaminics and bronchodilating agents. If used in combination with other substances, retinoid antagonists and said other substances can be administered separately or incorporated in effective amounts into one pharmaceutical composition.

In the scope of the present invention, the "pharmaceutically acceptable salts" includes any salt chemically permissible in the art for retinoid antagonists and applicable to human patients in a pharmaceutically acceptable preparation. Any such conventional pharmaceutically acceptable salt of retinoid antagonists can be utilized. Among the conventional salts which can be utilized, there are the base salts included, for example, alkali metal salts such as the sodium or potassium salt, alkaline earth metal salts such as the calcium or magnesium salt, and ammonium or alkyl ammonium salts.

In accordance with this invention the retinoid antagonists can also be administered in the form of its pharmaceutically acceptable hydrolyzable esters. Any pharmaceutically acceptable hydrolyzable ester can be used in the compositions and methods of this invention. Among the preferred esters are: the aromatic esters such as benzyl esters in which the benzyl moiety is unsubstituted or substituted with lower alkyl, halo, nitro, thio, or substituted thio; or lower alkyl esters, e.g. ethyl, t-butyl, cyclopentyl, cyclohexyl or cycloheptyl ester; or 9-fluorenylmethyl ester.

In the scope of the present invention the term "alkyl" means straight-chain, branched or cyclic alkyl residues, in particular those containing from 1 to 12 carbon atoms, such as methyl, ethyl, propyl, isopropyl, t-butyl, decyl, dodecyl, cyclopentyl, cyclohexyl, cycloheptyl and the like. The term "lower alkyl" means alkyl groups containing from 1 to 7 carbon atoms.

The aforementioned retinoid antagonists, the salts and esters thereof are useful especially in pharmaceutically acceptable oral or topical modes. These pharmaceutical compositions contain said active compound in association with a compatible pharmaceutically acceptable carrier material. Any conventional carrier material can be utilized. The carrier material can be organic or inorganic inert carrier material suitable for oral administration. Suitable carriers include water, gelatin, gum arabic, lactose, starch, magnesium stearate, talc, vegetable oils, polyalkylene-glycols, petroleum jelly and the like. Furthermore, the pharmaceutically active preparations may contain other pharmaceutically active agents. Additionally, additives such as flavoring agents, preservatives, stabilizers, emulsifying agents, buffers and the like may be added in accordance with accepted practices of pharmaceutical compounding.

The pharmaceutical preparations can be made up in any conventional form including: (a) solid form for oral administration such as tablets, capsules (e.g. hard or soft gelatine capsules), pills, sachets, powders, granules, and the like; and (b) preparations for topical administrations such as solutions, suspensions, ointments, creams, gels, micronized powders, sprays, aerosols and the like. Pharmaceutical preparations may be sterilized and/or may contain adjuvants such as preservatives, stabilizers, wetting agents, emulsifiers, salts for varying the osmotic pressure and/or buffers.

For topical administration to the skin or mucous membrane the aforementioned derivative is preferably prepared as ointments, tinctures, creams, gels, solution, lotions, sprays; aerosols and dry powder for inhalation, suspensions, shampoos, hair soaps, perfumes and the like. In fact, any conventional composition can be utilized in this invention. Among the preferred methods of applying the composition containing the agents of this invention is in the form of an ointment, gel, cream, lotion, spray; aerosol or dry powder for inhalation. A pharmaceutical preparation for opical administration to the skin can be prepared by mixing the aforementioned active ingredient with non-toxic, therapeutically inert, solid or liquid carriers customarily used in such preparation. These preparations generally contain 0.01 to 5.0 percent by weight, preferably 0.1 to 1.0 percent by weight, of the active ingredient, based on the total weight of the composition.

In preparing the topical preparations described above, additives such as preservatives, thickeners, perfumes and the like conventional in the art of pharmaceutical compounding of topical preparation can be used. In addition, conventional antioxidants or mixtures of conventional antioxidants can be incorporated into the topical preparations containing the afore-mentioned active agent. Among the conventional antioxidants which can be utilized in these preparations are included N-methyl-α-tocopherolamine, tocopherols, butylated hydroxyanisole, butylated hydroxytoluene, ethoxyquin and the like. Cream-base pharmaceutical formulations containing the active agent, used in accordance with this invention, are composed of aqueous emulsions containing a fatty acid alcohol, semi-solid petroleum hydrocarbon, ethylene glycol and an emulsifying agent.

Ointment formulations containing the active agent in accordance with this invention comprise admixtures of a semi-solid petroleum hydrocarbon with a solvent dispersion of the active material. Cream compositions containing the active ingredient for use in this invention preferably comprise emulsions formed from a water phase of a humectant, a viscosity stabilizer and water, an oil phase of a fatty acid alcohol, a semi-solid petroleum hydrocarbon and an emulsifying agent and a phase containing the active agent dispersed in an aqueous stabilizer-buffer solution. Stabilizers may be added to the topical preparation. Any conventional stabilizer can be utilized in accordance with this invention. In the oil phase, fatty acid alcohol components function as a stabilizer. These fatty acid alcohol components function as a stabilizer. These fatty acid alcohol components are derived from the reduction of a long-chain saturated fatty acid containing at least 14 carbon atoms. Also, conventional perfumes and lotions generally utilized in topical preparation for the hair can be utilized in accordance with this invention. Furthermore, if desired, conventional emulsifying agents can be utilized in the topical preparations of this invention.

For topical treatment of allergic rhinitis and allergic bronchial asthma nasal and inhalation aerosols are used. Formulations for such aerosols are described in *Drugs and Pharmaceutical Sciences*, Marcel Dekker, New York, 72: 547–574 (1996). Furthermore, the active compound can be delivered by dry powder inhalation. Such formulations and devices are described in *Pharmaceutical Technology*, June 1997, pp.117–125.

A preferred oral dosage form comprises tablets, pills, sachets, or capsules of hard or soft gelatin, methylcellulose or of another suitable material easily dissolved in the digestive tract. Each tablet, pill, sachet or capsule can preferably contain from about 5 to about 200 mg, more preferably from about 20 to about 100 mg, of active ingredient. The oral dosages contemplated in accordance with the present invention will vary in accordance with the needs of the individual patient as determined by the prescribing physician. Generally, however, a daily dosage of from 0.05 to 20 mg per kg of body weight, preferably 0.1 to 7 mg, and most preferably from about 0.3 mg to about 1.5 mg per kg of body weight of the patient is utilized. This dosage may be administered according to any dosage schedule determined by the physician in accordance with the requirements of the patient.

The dosage for treatment typically depends on the route of administration, the age, weight and disease condition of the individual. Suitable dosage forms are known in the art or can be easily obtained in a manner known per se. Formulations of lotions, gels, creams, sprays; aerosols and dry powder for inhalation, hard or soft gelatin capsules, tablets and sachets that are particularly suitable in the scope of the present invention or that can be easily adjusted in accordance with the above teaching are in the art.

EXPERIMENTAL METHODS

I. In Vitro Assay for IL-12 Induction by Retinoid Antagonists

THP-1 cells were obtained from American Tissue Culture Collection and cultured in complete medium. To assay for IL-12 production, THP-1 cells, $1.25 \times 10^6$ cells/ml, were stimulated with *S. aureus* Cowan strain (SAC) (1/1000) and human recombinant interferon-γ (huIFNγ) (1000 U/ml) [Ma et al., *J. Exp. Med.* 183: 147–157 (1996)]. Alternatively, $0.5 \times 10^6$ human peripheral blood mononuclear cells (PBMC) (1 ml culture in 48 well plates) were primed with huIFN-γ (1000 U/ml) for 16 hours at 37° C., and then stimulated with SAC (1/1000). Supernatants were collected after 48 hours, and freezed at −20° C. until assayed [Panina-Bordignon et al., *J. Clin. Invest.* 100: 1513–1519 (1997)].

IL-12 production was measured by specific enzyme linked immunosorbant assay (ELISA), using 20C2 antibody (rat anti human IL-12 heterodimer p40-p35), at 2.5 μg/ml in coating buffer, and peroxidase-conjugated 4D6 antibody (rat anti human IL-12) at 250 ng/ml in assay buffer as described [Zhang et al., *J. Clin. Invest.* 93: 1733–1739 (1994)]. Standard (recombinant human IL-12, 800 pg/ml to 6 pg/ml) and samples (100 μl) diluted in assay buffer were added to duplicate wells. Absorbance was read at 450–650 nm. The unknown IL-12 concentrations of the samples were read from the corresponding standard curve and multiplied by the corresponding dilution factor. Maximal IL-12 production varied between 200 and 400 pg/ml.

Lyophilized retinoid antagonists were diluted in DMSO under yellow light, on ice at a concentration of 2 mM. Serial dilutions (1 μM-1 pM) were prepared in complete RPMI medium. 10 μl of each dilution was added to 1 ml culture.

The results of the experiments indicate that the tested retinoid antagonists influence IL-12 production. In particular, the tested retinoid antagonists stimulate IL-12 production by activated human monocytes, see Table I and II.

TABLE I

Retinoid antagonists specifically enhance IL-12 production by activated monocytes

|  | nM | IL-12 (pg/ml) | IL-10 (pg/ml) | TNF-α (pg/ml) |
| --- | --- | --- | --- | --- |
| medium |  | 0 | <10 | <10 |
| SAC + IFN-γ |  | 120 | 1040 | 1840 |
| RAR α antagonist | 1000 | 251 | 1343 | 1912 |
| Compound A | 100 | 102 | 1050 | 1600 |
|  | 10 | n.d. | 1060 | 1392 |
| medium |  | 0 | <10 | <10 |
| SAC + IFN-γ |  | 126 | 1040 | 2000 |
| RAR αβγ antagonist | 1000 | 321 | 1116 | 2884 |
| Compound B | 100 | 205 | 983 | 2752 |
|  | 10 | 173 | 971 | 2592 |
| medium |  | 0 | <10 | <10 |
| SAC + IFN-γ |  | 120 | 1040 | 1840 |
| RXR antagonist | 1000 | 298 | 1700 | 1560 |
| Compound C | 100 | 161 | 1521 | 1812 |
|  | 10 | 106 | 1020 | 1484 |

TABLE II

Retinoid antagonists enhance IL-12 production by PBMC and THP-1 cells that have been primed with IFNγ and stimulated with SAC

| Compound | Receptor Specificity | Activity | Stimuli | Time* (hrs) | PBMC IL-12 | THP-1 (pg/ml) |
| --- | --- | --- | --- | --- | --- | --- |
| A | RARα | antagonist | IFNγ + | 0 | 503 | 306 |
|  |  |  | SAC | 16 | 401 | nd |
| B | RARα, β, γ | antagonist | IFNγ + | 0 | 371 | 364 |
|  |  |  | SAC | 16 | 367 | nd |
| C | RXR | antagonist | IFNγ + | 0 | 568 | 577 |
|  |  |  | SAC | 16 | 367 | nd |
| none |  |  | none |  | <12 | <2 |
|  |  |  | IFNγ + |  | 360 | 275 |
|  |  |  | SAC |  |  |  |

*retinoid antagonists (1 μg) were added at time 0 together with IFNγ or after 16 hours together with SAC.
Compound A p-[(E)-2-[3',4'-Dihydro-4',4'-dimethyl-7'-(heptyloxy)-2'H-1-benzothiopyran-6'-yl]propenyl]benzoic acid 1',1'-dioxide
Compound B 4-(7,7,10,10-Tetramethyl-1-pyridin-3-ylmethyl-4,5,7,8,9,10-hexahydro-1H-naphto[2,3-g]indol-3-yl)-benzoic acid
Compound C (2E,4E,6Z)-7-[2-Butoxy-3,5-bis(1,1-dimethylethyl)phenyl]-3-methyl-2,4,6-octatrienoic acid II. In Vitro Assay for Inhibition of Differentiation of Human Naive T Cells Into T Helper 2 (Th2) Cells by Retinoid Antagonists Naive T cells from cord blood were isolated and treated as described [Panina-Bordignon et al. *J. Clin. Invest.* 100:

1513–1519 (1997)]. Briefly, cord blood derived mononuclear cells were incubated with anti-CD45RA and anti-CD4 monoclonal antibodies. After a 20 minute incubation, cells were washed and incubated with goat anti-mouse Ig-coated magnetic beads. Positive cells were separated and seeded at $1 \times 10^6$ cells/ml in a 24 well plate, together with autologous adherent cells, PHA, and IL-4 in the presence or absence of p-[(E)-2-[3',4'-Dihydro-4',4'-dimethyl-7'-(heptyloxy)-2'H-1-benzothiopyran-6'-yl]propenyl]benzoic acid 1',1'-dioxide (Compound A) or (2E,4E,6Z)-7-[2-Butoxy-3,5-bis(1,1-dimethylethyl)phenyl]-3-methyl-2,4,6-octatrienoic acid (Compound C) at 1 mM for 5 days. Cells were then washed and put back in culture in the presence of IL-2 (100 U/ml). After 10 days, the cells were collected and restimulated with PMA (50 ng/ml) and ionomycin (1 μg/ml) for 4 hours. Brefeldin A (10 μg/ml) was added for the last 2 hours. Then the cells were fixed with 4% paraformaldehyde and permeabilized with saponin. Fixed cells were stained with FITC-anti IFNγ and PE-anti-IL-4mnAbs and subjected to cytofluorimetric analysis.

The results of the experiment indicate that the tested retinoid antagonists reduce the differentiation of naive T cells into IL-4-secreting Th2 cells. (Table III)

TABLE III

Suppression of IL-4 expression in
Th2 cells by retinoid antagonists

| | IL-4 expressing cells | |
|---|---|---|
| | % gated cells | % Th2 cells |
| Th2 | 26.32 | 100 |
| Th2 + Compound A | 10.8 | 41 |
| Th2 + Compound C | 8.5 | 32 |

III. Murine Model of Allergen-induced Airway Inflammation and Hyperresponsiveness C57BL/6 mice (8–9 weeks old) are actively sensitized to ovalbumin (OA) on day 0 and on day 14 by a intraperitoneal injection of 10 μg OA+1 mg Al(OH)$_3$ (gel suspension) in 0.2 ml sterile saline. On day 21, the mice were challenged with 5.0% OA aerosol for 18 minutes. The aerosol is generated by a De Vilbiss Ultra-Neb 90 ultrasonic nebulizer, the outlet of which is connected t6 a small plexiglass chamber containing the animals. The mice are dosed with the RXR antagonist Compound C (10 and 30 mg/kg intraperitoneally) daily for three days, 48 hours, 24 hours, and immediately prior to OA challenge. Animals are used on day 21.

Airway Inflammatory Cell Accumulation

On day 24, three days after the challenge with OA aerosol, animals are anesthetized with urethane (2.4 g/kg) and tracheotomized with a 23 gauge catheter. Lungs are lavaged with aliquots (2×1 ml) of sterile Hank's balanced salt solution without Ca++ and Mg++. Lavage fluid is recovered after 30 sec by gentle aspiration and pooled for each animal. Samples then are centrifuged at 2000 rpm for 15 minutes at 5° C. Red blood cells are lysed from the resulting pellet with 0.5 ml distilled water and the cells, remaining in the pellet are reconstituted with 5 ml HBSS. Samples are centrifuged a second time at 2000 rpm for 15 minutes at 5° C. The resulting pellet is suspended in 1 ml of HBSS. Total cell number is determined from an aliquot of the cell suspension using a hemocytometer. For cytological preparations, the cells are fixed on cytocentrifuged slides stained with a modified Wright's stain. Differential counts on at least 300 cells are made using standard morphological criteria to classify cells.

The results of the experiments indicate that the tested retinoid antagonists inhibit the allergen-induced accumulation of airway inflammatory cells (Table IV).

TABLE IV

Suppression of airway inflammatory cell
accumulation by retinoid antagonists in a mouse
model of allergen-induced airway inflammation

| | Cell Influx (cells/ml) | | | Percent of reduction | |
|---|---|---|---|---|---|
| | | Compound C | | Compound C | |
| | Vehicle | 10 mg/kg | 30 mg/kg | 10 mg/kg | 30 mg/kg |
| Total leukocytes | 795000 | 488000 | 271000 | 39% | 66% |
| Macrophages | 443000 | 289000 | 172000 | 35% | 62% |
| Eosinophils | 335000 | 176000 | 91000 | 48% | 73% |

Airway Hyperresponsiveness

On day 24, three days after the challenge with OA aerosol, animals are anesthetized with pentobarbital sodium (100 mg/kg, i.p.) and tracheotomized (PE-190). A jugular vein is cannulated with a sylastic tubing for i.v. drug delivery. Animals are placed in a whole body plethysmograph with a built-in pneumotachograph and mechanically ventilated ($V_f$=150/min., $V_t$=0.3ml; Model 683, Harvard Apparatus, S. Natic, Mass.) immediately following pancuronium bromide (0.1 mg/kg, i.v.) treatment. Tidal volume is obtained from an integration of the respiratory flow signal using a differential pressure transducer (Validyne DP 103-08, Northridge, Calif.). Transpulmonary pressure is measured with a differential pressure transducer (Validyne DP 45-30, Northridge. Calif.) as the difference between intratracheal pressure and intrapleural pressure (obtained from a cannula inserted into the intercostal space). Changes in lung resistance (cm H$_2$O/ml/s) to increasing doses of methacholine (30, 100, 300, 1000 μg/kg, i.v.) are calculated from transpulmonary pressure, tidal volume, and respiratory flow measurements using a Modular Instrument Signal Processing System (Malvern, Pa.).

The results of the experiments indicate that retinoid antagonists can prevent or reverse allergic airway inflammation and inhibit antigen-induced bronchoconstriction, typical for allergic airway diseases, such as allergic bronchial asthma.

Examples for formulations: capsules, tablets, sachets, lotions, gels, creams, aerosols and dry powder for inhalation. The active compounds in the following examples are p-[(E)-2-[3',4'-Dihydro-4,4'-dimethyl-7'-(heptyloxy)-2'H-1-benzothio-pyran-6'-yl]propenyl]benzoic acid 1,1'-dioxide or (2E,4E,6Z)-7-[2-Butoxy-3,5-bis(1,1-dimethylethyl) phenyl]-3-methyl-2,4,6-octatrienoic acid

EXAMPLE 1

| Lotion (solution) | | preferred |
|---|---|---|
| Active compound | 0.1–2.0 g | |
| Propylene Glycol | 5.00–20.00 g | 10.00 g |
| PEG-Glyceryl Cocoate* | 0.00–20.00 g | 10.00 g |
| dl-a-Tocopherol | 0.001–0.50 g | 0.02 g |
| Ascorbyl Palmitate | 0.01–0.20 g | 0.10 g |
| Propyl Gallate | 0.001–0.02 g | 0.002 g |
| Citric acid, anhydr.** | 0.00–0.20 g | 0.01 g |

-continued

| Lotion (solution) | | preferred | |
|---|---|---|---|
| Isopropanol*** | 40.00–90.00 g | 50.00 g | |
| Water, dem. ad | 100.00 g | 100.00 g | resp. ml |

*or other tensides
**or other complexing agents e.g. EDTA
***or other alcohols e.g. Ethanol

EXAMPLE 2

| Gel | | preferred | |
|---|---|---|---|
| Active compound | 0.1–2.0 g | | |
| Propylene Glycol | 5.00–20.00 g | 10.00 g | |
| PEG-Glyceryl Cocoate* | 0.00–20.00 g | 10.00 g | |
| dl-α-Tocopherol | 0.001–0.50 g | 0.02 g | |
| Ascorbyl Palmitate | 0.01–0.20 g | 0.10 g | |
| Propyl Gallate | 0.001–0.02 g | 0.002 g | |
| Citric acid, anhydr.** | 0.00–0.20 g | 0.01 g | |
| Isopropanol*** | 40.00–90.00 g | 50.00 g | |
| HPMC**** | 0.50–5.00 g | 3.00 g | |
| Preservative***** | q.s. | q.s. | |
| Water, dem. ad | 100.00 g | 100.00 g | resp. ml |

*or other tensides
**or other complexing agents e.g. EDTA
***or other alcohols e.g. Ethanol
****Hydroxypropyl Methylcellulose or other polymers e.g. neutralised Carbomer, Methyl Cellulose, Sodium Carboxymethylcellulose
*****Preservatives e.g., Paraben esters (methyl, ethyl, propyl, butyl). Sorbic Acid. Benzoic Acid

EXAMPLE 3

| Cream | | preferred |
|---|---|---|
| Active compound | 0.1–2.0 g | |
| Glycerol | 0.00–10.00 g | 5.00 g |
| Na₂ EDTA | 0.001–0.50 g | 0.03 g |
| Glycerides* | 5.00–20.00 g | 10.00 g |
| Cetyl Alcohol | 0.50–5.00 g | 1.00 g |
| Stearyl Alcohol | 0.50–5.00 g | 1.00 g |
| Glycerol mono Stearate | 1.00–8.00 g | 4.00 g |
| Ceteareth** | 0.50–5.00 g | 2.00 g |
| dl-α-Tocopherol | 0.001–0.50 g | 0.02 g |
| Preservative | q.s. | q.s. |
| Water, dem. ad | 100.00 g | 100.00 g |

*e.g. Caprylic/Capric/Triglyceride, Caprylic/Capric/Linoleic Triglycerides, natural glycerides, as well as e.g. Propylene Glycol, Dicaprylate/Dicaprate and waxes, such as Stearyl, Stearate, Oleyl Oleate, Isopropyl Myristate
**Ceteareth 5–30, or other emulsifiers such as Polysorbase 20–80, Sorbitane esters of fatty acids, fatty acid esters of PEG.
***Preservatives e.g., Paraben esters (methyl, ethyl, propyl, butyl). Sorbic Acid. Benzoic Acid

EXAMPLE 4

| Fill mass for soft gelatin capsules | |
|---|---|
| Active compound | 5.0–200.0 mg |
| Oil* | 1–3 parts |
| Wax mixture** | 1–5 parts |
| Fill volume | 1–6 minims |

*natural vegetable oils, e.g. soy oil, peanut oil, and artificial glycerides
**composition of natural and artificial waxes or partially hydrated fats 20 mg Soft Gelatin Capsules

| Ingredients | mg/capsule |
|---|---|
| Active compound | 20.000 |
| dl-α-Tocopherol | 0.028 |
| Hydrogenated Castor Oil | 4.200 |
| Caprylic/Capric/Stearic Triglyceride (Synthetic Triglyceride) | 56.000 |
| Triglyceride, Medium Chain | 199.772 |
| Total | 280.000 mg |

EXAMPLE 5

Hard Gelatine Capsules Containing 20 mg Active Substance

Composition: One Capsule Contains:

| | |
|---|---|
| Active compound | 20.0 mg |
| Gelatine Bloom 30 | 70.0 mg |
| Maltodextrin MD 05 | 108.0 mg |
| dl-α-Tocopherol | 2.0 mg |
| Sodium ascorbate | 10.0 mg |
| Microcrystalline cellulose | 48.0 mg |
| Magnesium stearate | 2.0 mg |
| (weight capsule content) | 260.0 mg |

Procedure:

The active substance is wet milled in a solution of gelatine, maltodextrin, dl-α-Tocopherol and sodium ascorbate.

The wet milled suspension is spray-dried.

The spray-dried powder is mixed with microcrystalline cellulose and magnesium stearate.

260 mg each of this mixture are filled into hard gelatine capsules of suitable size and color.

EXAMPLE 6

Tablet Containing 20 mg Active Substance

Composition:

Tablet Kernel:

| | |
|---|---|
| Active compound | 20.0 mg |
| Anhydrous lactose | 130.5 mg |
| Microcrystalline Cellulose | 80.0 mg |
| dl-α-Tocopherol | 2.0 mg |
| Sodium ascorbate | 10.0 mg |
| Polyvinylpyrrolidone K30 | 5.0 mg |
| Magnesium stearate | 2.5 mg |
| (Kernel weight) | 250.0 mg |

Film Coat:

| | |
|---|---|
| Hydroxypropyl methylcellulose | 3.5 mg |
| Polyethylenglycol 6000 | 0.8 mg |
| Talc | 1.3 mg |

|                    |        |
|--------------------|--------|
| -continued         |        |
| Irone oxide, yellow | 0.8 mg |
| Titanium dioxide   | 0.8 mg |
| (weight of the film) | 7.4 mg |

Procedure:

The compound is mixed with anhydrous lactose and microcrystalline cellulose. The mixture is granulated in water with a solution/dispersion of polyvinylpyrrolidone, dl-α-Tocopherol and sodium ascorbate.

The granular material is mixed with magnesium stearate and afterwards pressed as kernels with 250 mg weight.

The kernels are film coated with a solution/suspension of above-mentioned compositions.

EXAMPLE 7

Sachet Containing Active Substance

Composition:

| Active compound | 200.0 mg |
|-----------------|----------|
| Lactose, fine powder | 990.0 mg |
| Microcrystalline Cellulose | 1250.0 mg |
| Sodium Carboxymethyl cellulose | 14.0 mg |
| dl-α-Tocopherol | 5.0 mg |
| Sodium ascorbate | 20.0 mg |
| Polyvinylpyrrolidone K30 | 10.0 mg |
| Magnesium stearate | 10.0 mg |

EXAMPLE 8

Aerosol for Inhalation, Metered Dose Inhaler

| Active compound | 0.5% (0.1–2.0%) |
|-----------------|-----------------|
| Sorbitantrioleate | 5% |
| dl-α-Tocopherol | 0.4% |
| Propellant (mixture of Trichlorofluoromethane and Dichlorodifluoromethane) | 94.1% |

EXAMPLE 9

Dry Powder Inhaler

| Active compound* | 0.5 mg (0.1 mg–2.0 mg) |
|------------------|------------------------|
| Lactose monohydrate | 25 mg |

*jet-milled, spray-dried

What is claimed is:

1. A method of treating a T-helper cell type 2-mediated immune disease or a disease mediated by T-helper cell type 2-related cytokines, which comprises administering to a subject having a T-helper cell type 2-mediated immune disease or a disease mediated by T-helper cell type 2-related cytokines an effective amount of a compound selected from the group consisting of retinoid antagonists, pharmaceutically acceptable salts of retinoid antagonists, and pharmaceutically acceptable hydrolyzable esters of such retinoid antagonists and their salts, with the proviso that the T-helper cell type 2-mediated immune disease is not atopic dermatitis.

2. The method of claim 1, wherein the T-helper cell type 2-mediated immune disease is an immunoglobulin E-mediated allergic disease.

3. The method of claim 2, wherein the immunoglobulin E-mediated allergic disease is allergic rhinitis.

4. The method of claim 2, wherein the immunoglobulin E-mediated allergic disease is allergic bronchial asthma.

5. The method of claim 1, wherein the disease mediated by Th2-related cytokines is mediated by IL4 or IL-5.

6. The method of claim 1, wherein the compound is a retinoid antagonist of the formula:

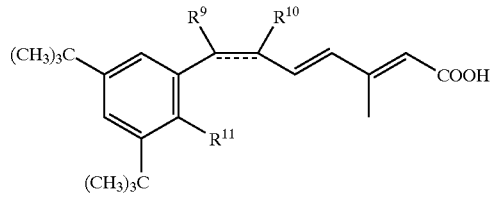

XV wherein—is a single bond or a double bond, when a double bond is present, $R^9$ is methyl and $R^{10}$ is hydrogen, and when a single bond is present, $R^9$ and $R^{10}$ taken together are methylene thus forming a cis-substituted cyclopropyl ring, and $R^{11}$ is $C_{1-4}$ alkoxy, or a pharmaceutically acceptable salt of such retinoid antagonist or a pharmaceutically acceptable hydrolyzable ester of such retinoid antagonist or its salt.

7. The method of claim 1, wherein the compound is a retinoid antagonist of the formula:

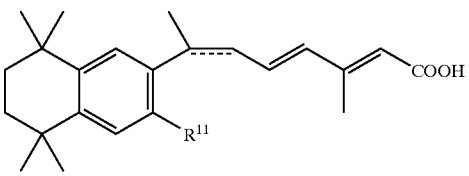

XVI wherein—is a single bond or a double bond and $R^{11}$ is $C_{1-4}$ alkoxy, or a pharmaceutically acceptable salt of such retinoid antagonist or a pharmaceutically acceptable hydrolyzable ester of such retinoid antagonist or its salt.

8. The method of claim 1, wherein the administering comprises oral administration.

9. The method of claim 8, wherein the oral administration is at a daily dosage of from about 0.05 mg to about 20 mg of the compound per kg of body weight of the subject.

10. The method of claim 9, wherein the oral administration is at a daily dosage of from about 0.3 mg to about 1.5 mg of the compound per kg of body weight of the subject.

11. The method of claim 8, wherein the oral administration comprises administering a tablet, capsule, pill or sachet containing from about 5 mg to about 200 mg of the compound.

12. The method of claim 11, wherein the oral administration comprises administering a tablet, capsule, pill or sachet containing from about 20 mg to about 100 mg of the compound.

13. The method of claim 1, wherein the administering comprises topical administration.

14. The method of claim 13, wherein the topical administration comprises administering an ointment, cream, lotion, or spray containing from about 0.01 percent to about 5.0 percent by weight of the compound.

15. The method of claim 14, wherein the topical administration comprises administering an ointment, cream, lotion, or spray containing from about 0.1 percent to about 1.0 percent by weight of the compound.

16. The method of claim 1, wherein the administering comprises inhalation.

17. The method of claim 16, wherein the inhalation comprises administering a nasal aerosol, aerosol for inhalation, or dry powder for inhalation containing from about 0.01 percent to about 5.0 percent by weight of the compound.

18. The method of claim 17, wherein the inhalation comprises administering a nasal aerosol, aerosol for inhalations, or dry powder for inhalation containing from about 0.1 percent to about 1.0 percent by weight of the compound.

19. The method of claim 1, wherein the compound is a retinoid antagonists or a alkali metal salt, alkaline earth metal salt, benzyl ester, lower alkyl ester, or 9-fluorenylmethyl ester thereof.

* * * * *

UNITED STATES PATENT AND TRADEMARK OFFICE
CERTIFICATE OF CORRECTION

PATENT NO. : 6,610,742 B1
DATED : August 26, 2003
INVENTOR(S) : Werner Bollag et al.

It is certified that error appears in the above-identified patent and that said Letters Patent is hereby corrected as shown below:

Title page,
Item [73], Assignee, delete "Hoffman-La Roche Inc." and insert -- Hoffmann-La Roche Inc. --.

Column 16,
Lines 22 and 41, delete "—" and insert -- ---- --.

Signed and Sealed this

Thirtieth Day of December, 2003

JAMES E. ROGAN
*Director of the United States Patent and Trademark Office*